United States Patent
Bosworth et al.

(10) Patent No.: US 6,596,923 B1
(45) Date of Patent: *Jul. 22, 2003

(54) **METHODS AND COMPOSITIONS TO IDENTIFY SWINE GENETICALLY RESISTANT TO F18 *E. COLI* ASSOCIATED DISEASES**

(75) Inventors: Brad T. Bosworth, Littleton, NC (US); Peter Vögeli, Zurich (CH)

(73) Assignees: Biotechnology Research & Development Corp., Peoria, IL (US); The United States of America as represented by the Secretary of Agriculture, Washington, DC (US); Swiss Federal Institute of Technology, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/443,766

(22) Filed: Nov. 19, 1999

Related U.S. Application Data

(60) Provisional application No. 60/047,181, filed on May 20, 1997.

(51) Int. Cl.[7] .................. A01K 67/00; A01K 67/033; C07H 21/02; C07H 21/04; A61K 49/00
(52) U.S. Cl. .................. 800/8; 536/23.1; 536/23.5; 424/9.1
(58) Field of Search .................. 435/4, 6, 7.2, 7.32, 435/7.37; 800/8; 536/23.1, 23.5; 424/9.1

(56) References Cited

U.S. PATENT DOCUMENTS

| 5,358,649 A | 10/1994 | MacLennan et al. ........... 435/6 |
| 5,552,144 A | 9/1996 | Samuel et al. ........... 424/236.1 |
| 5,625,124 A | 4/1997 | Falk et al. ........... 800/2 |

FOREIGN PATENT DOCUMENTS

| WO | WO 86/04604 | 8/1986 |
| WO | WO 94/13811 | 6/1994 |

OTHER PUBLICATIONS

Duchet–Suchaux et al., Susceptibility of Chinese Meishan and European Large White pigs to enterotoxgenic *Escherichia coli* strains bearing colonization factor K88, 987P, K99, or F41, Jan. 1991, Am J Vet Res, vol. 52, No. 1, pp. 40–49.*

Bertin et al, Relationship between virulence and adherence of various enterotoxigenic *Escherichia coli* strains to isolated intestinal epithelial cells from Chinese Meishan and European Large White pigs, Jan. 1991, Am J Vet Res, vol. 52, No. 1 pp. 45–49.*

Kennan, R.M., et al. (1995) "Confirmation that DNA Encoding the Major Fimbrial Subunit of Av24 Fimbriae is Homologous to DNA Encoding the Major Fimbrial Subunit of F107 Fimbriae." *Microbial Pathogenesis* 18: 67–72.

Meijerink, E., et al. (1997) "Two α(1,2) Fucosy Itransferase Genes on Porcine Chromosome 6q11 are Closely Linked to the Blood Group Inhibitor (S) and *Escherichia coli* F18 Receptor (*ECF18R*) Loci." *Mammaliam Genome* 8: 736–741.

Rutter, et al. (1975) "A Genetic Basis for Resistance to Enteric Disease Caused by *E. Coli.*" *Nature* 257(5522): 135–6.

Schultz, L., et al. (1997) "Detection of the Fimbrial Gene F18 (F107) From Swine Enteritis *Escherichia Coli.*" *Mechanisms in the Pathogenesis of Enteric Diseases*. Paul et al. eds. Plenium Press. New York pp. 95–97.

Vögeli, p., et al. (1996) "Gene Specifying Receptors for F18 Fimbriated *Escherichia Coli*, Causing Oedema Disease and Postweaning Diarrhoea in Pigs, Map to Chromosome 6." *Anim Genet* 27: 321–328.

Bosworth, B.T. et al. (1996) "Vaccination With Genetically Modified Shiga–Like Toxin IIe Prevents Edema Disease in Swine" *Infect and Immun* 64(1): 55–60.

Cohney, S. et al. (1996) "Molecular Cloning of the Gene Coding for pig α1→2fucosyltransferase" *Immunogenet* 40: 76–79.

Devereux, J. et al. (1984) "A Comprehensive Set of Sequence Analysis Programs for the VAX" *Nucl Acids Res* 12(1): 387–395.

Fujii, J. et al. (1991) "Identification of a Mutation in Porcine Ryanodine Receptor Associated with Malignant Hyperthermia" *Science* 253: 448–451.

Gaffney, R.A. et al. (1994) "Effect of Lewis Blood Group Antigen Expression on Bacterial Adherence to COS–1 Cells" *Infect and Immun* 62(7): 3022–3026.

(List continued on next page.)

Primary Examiner—Deborah Crouch
Assistant Examiner—Joseph Woitach
(74) Attorney, Agent, or Firm—Barnes & Thornburg; Alice O. Martin

(57) ABSTRACT

The present invention provides non-invasive methods and compositions to differentiate, with a high level of sensitivity and specificity, swine that are genetically susceptible to diseases associated with F18 *E. coli* infection, from resistant swine. DNA polymorphisms in the swine alpha (1,2) fucosyltransferase 1 (FUT1) gene were used to differentiate resistant from susceptible swine. The invention includes a polypeptide with amino acid substitutions, encoded by the nucleotide polymorphisms, a molecular diagnostic assay, and a kit for the differentiation, of *E. coli* F18-adhesion resistant, heterozygous (carrier) and homozygous susceptible pigs. The molecular test identifies susceptibility to oedema disease and postweaning diarrhea with high sensitivity and specificity, therefore, is useful to swine breeder in their effort to enhance for resistance. Information on the polymorphisms of the present invention provides insight into causation and treatment of *E. coli* associated intestinal disorders.

1 Claim, 1 Drawing Sheet

OTHER PUBLICATIONS

Information Disclosure Statement (Oct. 27, 1998).

Kelly, R.J. et al. (1994) "Molecular Basis for H Blood Group Deficiency in Bombay ($O_h$) and para–Bombay Individuals" *Proc Natl Acad Sci* 91: 5843–5847.

Meijerink, E et al. (1997) "Two α(1,2) fucosyltransferase Genes on Porcine Chromosome 6q11 are Closely Linked to the Blood Group Inhibitor (S) and *Escherichia coli* F18 Recetpor (*ECF18R*) Loci" *Mammal Genome* 8: 736–741.

Nagy, B. et al. (1992) "Susceptibility of Porcine Intestine to Pilus– Mediated Adhesion by Some Isolates of Piliated Enterotoxigenic *Escherichia coli* Increases with Age" *Infect and Immun* 60(4): 1285–1294.

Vögeli, P. et al. (1996) "Genes Specifying Receptors for F18 Fimbriated *Escherichia coli*, Causing Oedema Disease and Postweaning Diarrhoea in Pigs, Map to Chromosome 6" *Anim Genet* 27: 321–328.

Vögeli, P. et al. (1997) "Ein Molekularer Test für Nachweis des *E.–coli*–F18–Rezeptors:ein Durchbruch im Kampf genen Öedemkrankheit und Absetzdurchfall beim Schwein" *Schweiz Arch Tiereilk* 139(11): 479–484.

\* cited by examiner

FIGURE 1

```
                         M   W   V   P   S   R   R   H   L   C   L   T   F   L   L   V   C    17
CT  CGA GCC ATG TGG GTC CCC AGC CGC CGC CAC CTC TGT CTG ACC TTC CTG CTA GTC TGT            59
 V   L   A   A   I   F   F   L   N   V   Y   Q   D   L   F   Y   S   G   L   D             37
GTT TTA GCA GCA ATT TTC TTC CTG AAC GTC TAT CAA GAC CTC TTT TAC AGT GGC TTA GAC           119
 L   L   A   L   C   P   D   H   N   V   V   S   S   P   V   A   I   F   C   L             57
CTG CTG GCC CTG TGT CCA GAC CAT AAC GTG GTA TCA TCT CCC GTG GCC ATA TTC TGC CTG           179
 A   G   T   P   V   H   P   N   A   S   D   S   C   P   K   H   P   A   S   F             77
GCG GGC ACG CCG GTA CAC CCC AAC GCC TCC GAT TCC TGT CCC AAG CAT CCT GCC TCC TTT           239
 S   G   T   W   T   I   Y   P   D   G   R   F   G   N   Q   M   G   Q   Y   A             97
TCC GGG ACC TGG ACT ATT TAC CCG GAT GGC CGG TTT GGG AAC CAG ATG GGA CAG TAT GCC           299
 T   L   L   A   L   A   Q   L   N   G   R   Q   A   F   I   Q   P   A   M   H            117
ACG CTG CTG GCC CTG GCG CAG CTC AAC GGC CGC CAG GCC TTC ATC CAG CCT GCC ATG CAC           359
 A   V   L   A   P   V   F   R   I   T   L   P   V   L   A   P   E   V   D   R            137
GCC GTC CTG GCC CCC GTG TTC CGC ATC ACG CTG CCT GTC CTG GCG CCC GAG GTA GAC AGG           419
 H   A   P   W   R   E   L   E   L   H   D   W   M   S   E   D   Y   A   H   L            157
CAC GCT CCT TGG CGG GAG CTG GAG CTT CAC GAC TGG ATG TCC GAG GAT TAT GCC CAC TTA           479
 K   E   P   W   L   K   L   T   G   F   P   C   S   W   T   F   F   H   H   L            177
AAG GAG CCC TGG CTG AAG CTC ACC GGC TTC CCC TGC TCC TGG ACC TTC TTC CAC CAC CTC           539
 R   E   Q   I   R   S   E   F   T   L   H   D   H   L   R   Q   E   A   Q   G            197
CGG GAG CAG ATC CGC AGC GAG TTC ACC CTG CAC GAC CAC CTT CGG CAA GAG GCC CAG GGG           599
 V   L   S   Q   F   R   L   P   R   T   G   D   R   P   S   T   F   V   G   V            217
GTA CTG AGT CAG TTC CGT CTA CCC CGC ACA GGG GAC CGC CCC AGC ACC TTC GTG GGG GTC           659
 H   V   R   R   G   D   Y   L   R   V   M   P   K   R   W   K   G   V   V   G            237
CAC GTG CGC CGC GGG GAC TAT CTG CGT GTG ATG CCC AAG CGC TGG AAG GGG GTG GTG GGT           719
 D   G   A   Y   L   Q   Q   A   M   D   W   F   R   A   R   Y   E   A   P   V            257
GAC GGC GGT TAC CTC CAG CAG GCT ATG GAC TGG TTC CGG GCC CGA TAC GAA GCC CCC GTC           779
 F   V   V   T   S   N   G   M   E   W   C   R   K   N   I   D   T   S   R   G            277
TTT GTG GTC ACC AGC AAC GGC ATG GAG TGG TGC CGG AAG AAC ATC GAC ACC TCC CGG GGG           839
 D   V   I   F   A   G   D   G   R   E   A   A   P   A   R   D   F   A   L   L            297
GAC GTG ATC TTT GCT GGC GAT GGG CGG GAG GCC GCG CCC GCC AGG GAC TTT GCG CTG CTG           899
 V   Q   C   N   H   T   I   M   T   I   G   T   F   G   F   W   A   A   Y   L            317
GTG CAG TGC AAC CAC ACC ATC ATG ACC ATT GGC ACC TTC GGC TTC TGG GCC GCC TAC CTG           959
 A   G   G   D   T   I   Y   L   A   N   F   T   L   P   T   S   S   F   L   K            337
GCT GGT GGA GAT ACC ATC TAC TTG GCT AAC TTC ACC CTG CCC ACT TCC AGC TTC CTG AAG          1019
 I   F   K   P   E   A   A   F   L   P   E   W   V   G   I   N   A   D   L   S            357
ATC TTT AAA CCC GAG GCT GCC TTC CTG CCC GAG TGG GTG GGC ATT AAT GCA GAC TTG TCT          1079
 P   L   Q   M   L   A   G   P   *                                                        365
CCA CTC CAG ATG TTG GCT GGG CCT TGA ACC AGC AGG AGC CTT CTG GAA TAG CTC GGT              1139
CAA CCC AGG GCC AGC GTT ATG GGT CTC CGG AAG CCC GAG TAA CTT CCG GAG ATG CTG TGG          1199
GTC CTG TAG CAG GCT GGA CAC TTA TTT CAA GAG TGA TTC TAA TTG GCT GGA CTC AGA GGA          1259
AAC CCT GCA G                                                                             1269
```

METHODS AND COMPOSITIONS TO IDENTIFY SWINE GENETICALLY RESISTANT TO F18 E. COLI ASSOCIATED DISEASES

This application claims priority to PCT/US98/10318 filed May 20, 1998, which claims priority from U.S. Provisional Application 60/047,181 filed May 20, 1997, now abandoned.

Compositions and non-invasive methods are provided for the identification of swine genetically resistant to E. Coli bacteria supplied with fimbriae F18. DNA polymorphisms in the swine alpha (1,2) fucosyltransferase (FUT1) gene were identified that differentiate resistant from susceptible swine and provide a diagnostic test useful for swine breeders.

A major problem in breeding swine is to keep them disease-free. Intestinal disorders postweaning are a particular problem. A limited number of serotypes of toxigenic Escherichia (E.) Coli strains are the causative agents of oedema disease and postweaning diarrhea in swine which induce serious economic losses, especially among piglets aged 4 to 12 weeks, in swine breeding farms all over the world. The typical symptoms of oedema disease are neurological signs such as ataxia, convulsions and paralysis. At post mortem examination, oedema is typically present at characteristic sites such as eyelids and forehead, stomach wall and mesocolon. The diseases are cause be Shiga-like toxin-II variant and enterotoxins LT, Sta, Stb respectively, produced by E. coli that colonize the surface of the small intestine without effecting major morphological changes of the enterocytes (cells in the intestine). Certain types of bacterial E. coli strains, F18, F4 and K88 are major lethal villains in this regard. "Oedema disease of pigs is an enterotoxaemia characterized by generalized vascular damage. The latter is cause by a toxin, Shiga-like toxin II variant, produced by certain strains of E. coli" (Bertschinger et al., 1993). The E. coli are distinguished by their pili types, a group of adhesive fimbriae that are related are designated e.g., K88 or F18 (Vogeli et al., 1997).

Not all swine succumb to E. coli infections. Colonization depends on adherence of the bacteria to the enterocytes which is mediated by the bacterial fimbriae designated e.g., K88 or F18. Susceptibility to adhesion, i.e. expression of receptors in swine for binding the fimbriae, has been shown to be genetically controlled by the host and is inherited as a dominant trait with, in the case of F18, B being the susceptibility allele and b the resistance allele. (Vogeli et al., 1996; Meijerink et al., 1996). The genetic locus for this E. coli F18-receptor (ECF18R) has been mapped to porcine chromosome 6 (SSC6), based on its close genetic linkage to the S locus and other loci of the halothane (HAL) linkage group on chromosome 6. The receptor for K88 E. coli is on chromosome 13.

The mechanism for resistance appears to be that intestinal borders in resistant animals are not colonized by E. coli, i.e., the bacteria do not adhere to intestinal walls of resistant swine. Glycoprotein receptors in the brush border membrane of the intestine were shown to be responsible for the differences between adhesive and non-adhesive phenotypes related to some E. coli, therefore, the genotype of the host swine determines resistance. The fimbriated bacteria also have been studied. (WO 9413811).

Current methods of identifying swine that are resistant to F18 E. coli associated diseases are either to 1) collect intestinal samples from swine at slaughter and perform the microscopic adhesion test, 2) challenge the animals with virulent E. coli ("colonization test"), or 3) perform blood typing of the A-O(S) blood group system. The first two methods are not practical for identifying resistant animals for use as breeding stock. Although the blood typing method does identify resistant animals, the test is unable to determine whether susceptible animals are homozygous or heterozygous for susceptibility. Knowledge of the genotype of animals with regard to these alleles (conditions of a gene) is essential to develop a successful breeding program. The purpose of the breeding program is to produce swine that are resistant to F18 E. coli associated diseases that decimate stock post-weaning.

In one publication the authors stated, in reference to oedema disease in swine, that "Searches are underway for appropriate genetic markers . . . " (Bertschinger et al., 1993, page 87) and, citing Walters and Sellwood, 1982:

Breeding resistant swine is an attractive method for prevention of diseases for which an effective prophylaxis is not available. The feasibility of this approach will depend on the prevalence of the gene(s) encoding resistance in the pig population improved methods for the detection of resistant pigs, and absence of negative genetic traits co-selected with this resistance.

A genetic "marker" locus is a coding or non-coding locus that is close to a genetic locus of interest, but is not necessarily the locus itself. Detectable phenotypes include continuous or discontinuous traits, e.g. restriction length fragment polymorphisms, production traits, bacterial adhesion traits, colorimetric or enzymatic reactions, and antibiotic resistance. The S locus controls expression of the A and O blood group antigens. Swine homozygous recessive at the S locus do not express either A or O blood group antigens. A similar condition exists in humans and is due to mutations in the alpha (1,2) fucosyltransferase gene which encodes the human blood group H (Kelly et al., 1994; see also WO 9628967). The porcine alpha (1,2) fucosyltransferase gene of swine has recently been sequenced (Cohney et al., 1996). This gene is very likely the gene present at the S locus in swine.

The blood group H and Se loci have been mapped genetically and physically to human chromosome 19q13.3. This region is evolutionarily conserved, containing genes homologous to the HAL linkage group of genes in pigs. The blood group H encoding gene is the so called FUT1 whereas the Se gene is equivalent to the FUT2 gene. FUT1 determines H antigen expression in the erythroid cell lineage, whereas FUT2 regulates expression of the H antigen in the secretory epithelia and saliva. Conservation of the FUT1 gene has been shown in lower mammals such as rat and rabbit, and mRNA expression has been shown in rabbit brain tissue and rat colon. In all these species two types of alpha (1,2) fucosyltransferase genes have been reported which are structurally very similar to the human FUT1 and FUT2 genes, but in particular the FUT1 homologous genes show a species specific expression pattern. In humans the FUT1 gene is responsible for synthesis of H antigens in the precursors of erythrocytes. However, in pigs erythrocytes passively adsorb H-like antigens from the serum, as is the case for the human Lewis antigens. In pigs all H-like antigens are related to exocrine secretory tissues, and expression of the FUT2 (Secretor) gene is seen in secretory tissue of other animal species. Therefore, expression of the porcine A-O blood group determinants which cross-react with anti-human blood group H and A antibodies might be influenced by the FUT2 gene.

Further information about blood groups and *E. coli* swine diseases include that carbohydrate structures of blood group antigens mediate the adhesion of some pathogenic microorganisms to host tissues, e.g. *Helicobacter pylori* adhere to Lewis[b] blood group antigens, and *E. coli* causing urinary tract infections adhere to blood group P substance. Genes encoding glycosyltransferases that are responsible for the formation of the blood group specific carbohydrate structures, therefore, represent candidate genes for the control of bacterial colonization by the host. The localization of these genes is in the same chromosomal region as the locus responsible for adhesion/non-adhesion of F18 positive *E. coli* in the swine small intestine. Swine do not express blood group antigens A and O until after weaning, this is the same time that they become susceptible to disease caused by F18 *E. coli*.

New methods of diagnosis and treatment are needed for *E. coli* related intestinal diseases in swine. Detection of a genetic mutation was proposed as a diagnostic test for some swine disorders (malignant hypothermia) (Fujii et al., 1991; U.S. Pat. No. 5,358,649), but polymorphic markers were not reported for diagnosis. Vaccines to develop resistance to *E. coli* colonization were described (U.S. Pat. No. 5.552,144; WO 8604604), but are unlikely to be a preferred method to prevent the *E. coli* disease because of difficulties in administering live vaccine orally to newborn swine, and because of regulatory restrictions. Antibiotics are available for treatment, but there is no successful prophylaxis.

SUMMARY OF THE INVENTION

The compositions and non-invasive methods of the present invention provide detection and elimination of swine that are susceptible to *E. coli* associated diseases. A non-invasive method for identifying a swine that is resistant to intestinal colonization by *E. coli* F18 includes the following steps: determining whether a genetic polymorphism associated with resistance to colonization is in a biological sample from the swine; and inferring that the swine is resistant if the swine is homozygous for the polymorphism.[1]

[1] A polymorphism is a change in a nucleotide sequence that exists in a population due to mutation.

More particularly, the method is determining in a biological sample from the swine whether the nitrogen base at position 307 in the alpha (1,2) fucosyltransferase gene of the swine is only adenine or only guanine; and identifying the swine as resistant if the only nitrogen base at position 307 is adenine.

To determine whether a polymorphism is present in a biological sample, restriction fragment length polymorphisms are analyzed on a gel that separates them by molecular weight. Restriction endonucleases are enzymes that reproducibly cut nucleic acid molecules at specific sites, resulting in nucleic acid fragments of different molecular weights, depending on the location of the cuts.

The invention also relates to a method for breeding swine to be resistant to *E. coli* associated diseases by selecting for breeding swine that have a genetic polymorphism in the alpha (1,2) fucosyltransferase 1 gene that identifies them as swine that are resistant to *E. coli* related intestinal diseases; and breeding the selected swine.

An aspect of the invention is a DNA molecule which is polymorphic for the alpha (1,2) fucosyltransferase 1 gene in swine, in particular a sequence in accordance with FIG. 1. Other aspects of the invention are molecules with nucleotide sequences complementary to that of FIG. 1.

An aspect of the invention is an isolated DNA molecule with a substitution of adenine for guanine in position 307. This molecule may also bond a substitution of adenine for guanine in position 857. Other isolated DNA molecules of the present invention include those with a mutation at nucleotide position 229 of the sequence of FIG. 1, wherein the codon CTT is changed to TTT, encoding for the amino acid phenylalanine instead of leucine. A mutation at nucleotide position 714 is from GAT→GAC, but there is no accompanying amino acid substitution in the encoded product.

Polypeptides encoded by the DNA molecules of the present invention and having alpha (1,2) fucosyltransferase activity are also aspects of the invention.

A molecular assay for detecting *E. coli* F18 receptors in swine is to (a) isolate DNA from porcine nucleated cells; (b) amplify the DNA in a polymerase chain reaction (PCR) using oligonucleotides as primers which are complementary to a DNA sequence of the porcine alpha (1,2) fucosyltransferase gene 1; (c) perform a restriction enzyme digest with at least one restriction enzyme e.g., CfoI; (d) separate the resulting fragments by gel electrophoresis; and (e) determine the respective numbers and lengths of fragments on the gel; and (f) determine from the numbers and length of fragments of F18, which receptors are present in the porcine cells. Use of the larger amplified fragments disclosed herein for restriction length polymorphism analysis (RFLP), rather than smaller fragments, is less expensive because the DNA bands can be run on agarose gels of relatively low concentration. Also, to produce some of the fragments, only one restriction enzyme is needed for a constant restriction site adjacent to the variable diagnostic site.

A kit for detecting polymorphisms associated with *E. coli* F18 receptors uses oligonucleotides in separate containers which are complementary to a DNA sequence of the porcine alpha (1,2) fucosyltransferase gene 1 that distinguishes resistant from sensitive swine. The test can be performed on swine of any age.

The polymorphisms are also useful to develop drugs to treat swine that have *E. coli*-associated disease. A mutated form of porcine alpha 1,2 fucosyltransferase could interfere with the normal enzyme, preventing it from producing the intestinal receptor for F18.

BRIEF DESCRIPTION OF THE DRAWINGS

FIG. 1 shows the nucleotide sequence (FUT1) (below) and the predicted amino acid sequence (above) of the swine α1→2 fucosyltransferase polymorphism of the present invention using the one-letter amino acid code. The solid double line below the amino acid sequences (=) is the putative transmembrane region; the dotted line below the amino acid sequence shows three potential N-linked glycosylation sites ( . . . ).

☐ is where an adenine (A) is substituted for guanine (G) in resistant swine.

*Indicates the termination codon.

Abbreviations for the amino acid residues are as follows: A, Ala; C, Cys; D, Asp; E, Glu; F, Phe; G, Gly; H, His; I, Ile; K, Lys; L, Leu; M, Met; N, Asn; P, Pro; Q, Gin; R, Arg; S, Ser; T, Thr; V, Val; W, Trp; and Y, Tyr.

DESCRIPTION OF THE PREFERRED EMBODIMENT

Molecular analysis of DNA polymorphisms associated with resistance of swine to *E. coli* associated diseases facilitated diagnostic assays to select resistant pigs for breeding. Resistant pigs differ from sensitive pigs at the *E. coli* F18 receptor locus as identified by the polymorphic markers of the present invention.

The present invention provides non-invasive methods and compositions to distinguish with a high level of sensitivity and specificity, swine that are genetically susceptible to diseases associated with F18 *E. coli* infection from resistant swine. A DNA polymorphism in the swine alpha (1,2) fucosyltransferase (FUT1) gene was identified that differentiates resistant from susceptible swine. The polymorphism arose by a mutation (change) in a nucleotide sequence leading to a new allele. An allele is a condition of a gene. In a population there may be many alleles of a gene differing by nitrogen base substitutions, presumably caused by mutations in an ancestral DNA molecule. The coexistence in a population of more than one allele (sometimes referred to as a "variant") is called a genetic polymorphism. Loci at which more than one allele may exist as apparently stable components of a population, is a polymorphic locus. Usually, one of the polymorphic loci is at a low frequency in the population.

As determined from a biological sample, preferably blood, the resistant swine have a polymorphism in their genomes in which the only base detected at position 307 (see FIG. 1) in the nucleotide sequence is adenine, whereas the base in the same position in homozygous susceptible swine is guanine. Heterozygous swine will show both types of DNA and will be susceptible. The polymorphism is a variation of a porcine gene sequence (Cohney et al. 1996).

Genetic linkage analysis was performed on families of swine and genetic associations between polymorphisms in FUT1 and disease resistance in outbreed swine were determined. According to the present invention, polymorphisms have been found in the alpha (1,2) fucosyltransferase 1 gene (FUT1). A polymorphism that has a single nucleotide base substitution at position 307 was used to establish a close linkage between the fucosyltransferase gene and the S-system, the ECF18R locus and other loci of the HAL linkage group.

The detection of the close linkage of the mutation at FUT1 and ECF18R allowed a molecular test to be developed for the identification of *E. coli* F18 adhesion resistant, heterozygous (carrier) and homozygous susceptible pigs. This diagnostic test identifies, with high sensitivity and specificity, pigs that are susceptible to oedema disease and postweaning diarrhea. The incidence of the polymorphisms of the present invention differs among swine breeds. Vogeli, et al. (1997) presented frequencies of the M307 allele in 5 pig breeds from herds that were not related to one another. The availability of the diagnostic test for the polymorphism of the present invention provides breeders with the opportunity to effectively eliminate the ECF18R susceptible allele from their swine herds, thereby eliminating a prerequisite for *E. coli* F18 bacterial adhesion causing oedema disease and postweaning diarrhea.

The present invention further includes nucleotide sequences that are variants of a sequence of the alpha (1,2) fucosyltransferase gene 1 representing the various polymorphisms at bp 307, and diagnostic molecular based kits to identify polymorphisms in the alpha (1,2) fucosyltransferase gene.

In order to obtain candidate genes for the *E. coli* F18 receptor locus (ECF18R) 5 cosmids and one genomic clone containing the gene were isolated containing the alpha (1,2) fucosyltransferase genes, FUT1 and FUT2 (Meijerink et al., 1997), from a porcine genomic library. Mapping by fluorescence in situ hybridization placed all these clones in band q11 of porcine chromosome 6 (SSC6q11). Sequence analysis of the cosmids resulted in the characterization of (a) an open reading frame (ORF), 1098 base pairs in length, that is 82.3% identical to the human FUT1 sequence, and (b) a second ORF, 1023 base pairs in length which is 85% identical to human FUT2 sequence. The FUT1 and FUT2 loci therefore seem to be porcine equivalents of the human blood group H and the Secretor locus. Direct sequencing of the two ORFs in swine either susceptible or resistant to adhesion and colonization by F18 fimbriated *E. coli* (ECF18R) revealed two polymorphisms at base pair 307 (M307) and base pair 857 (M857) of the FUT1 ORF. The nucleotide positions are numbered from ATG (encoding methionine). Analysis of these mutations in 34 matings of Landrace families with 221 progeny showed close linkage with the locus controlling resistance and susceptibility to *E. coli* F18 adhesion and colonization in the small intestine (ECF18R) and with the locus of the blood group inhibitor S. Therefore, the M307 mutation is a good marker for marker-assisted selection of *E. coli* F18 adhesion resistant animals. Another mutation at nucleotide position 229 was found leading to a polymorphism in which the codon encoding leucine (CTT) was changed to TTT (encoding phenylalanine). A mutation at position 714(GAT→GAC) (encoding aspartic acid) did not produce an amino acid substitution. No polymorphisms were identified in FUT2 that differentiated susceptible and resistant pigs.

EXAMPLES

The following examples provide embodiments of the invention.

Example 1

An Assay For Resistant Swine

The polymorphisms of the present invention are easily identified using PCR-RFLP tests. One embodiment of the tests used a 160 bp fragment of porcine alpha (1,2) fucosyltransferase 1 amplified using PCR with the following primers; 5'CCAACGCCTCCGATTCCTGT3' (SEQ ID NO:1) and 5'GTGCATGGCAGGCTGGATGA3' (SEQ ID NO:2). Preferred PCR conditions for this embodiment are 25 cycles at the following times and temperatures: 94° C., 30 sec; 60° C., 45 sec; 72° C., 90 sec. The amplified DNA from resistant swine was digested by the restriction enzyme Hgal, but was not digested by the restriction enzyme HinPI. The amplified DNA from homozygous susceptible swine was digested by the restriction enzyme HinPI. The amplified DNA from heterozygous susceptible swine was partially digested by both enzymes.

Alternatively, DNA was isolated from porcine nucleated cells according to standard procedures. Direct sequencing of porcine FUT1 and FUT2 sequences and their flanking regions in animals of different ECF18R genotype (Bb, bb) resulted in the identification of two G→A transitions at positions 307 and 857 (termed M307 and M857, respectively) of the FUT1 ORF. The M307 transition eliminates a restriction site for CfoI. Amplification of DNA isolated from porcine nucleated cells was performed according to standard procedures with primers P6 and P11 (3 min at 95° C., 30 cycles of 30 sec at 95° C., 30 sec at 56° C. and 30 sec at 72° C., followed by a 7 min final extension at 72° C.) followed by CfoI digestion and separation on a 3% agarose gel resulted in a restriction fragment length polymorphism (RFLP). Homozygous M307$^{AA}$ animals showed 2 bands. Homozygous M307$^{GG}$ animals showed 93-, 241- and 87 bp fragments. Heterozygous animals showed all four fragments.

Example 2

Sensitivity And Specificity Of An Assay Using Alpha (1,2) Fucosyltransferase In Detecting Swine Resistant To F18 *E. Coli*

A study was conducted to determine the association between disease resistance and the polymorphism at position 307 of the FUT1 gene. 183 weaned swine (ranging in ages 2–6 months) were obtained from six different breeding herds. Only one of these herds was known to contain resistant animals before the start of the study, and this herd is known to have a high incidence of porcine stress syndrome. The other 5 herds had no evidence of porcine stress syndrome, and the incidence of disease resistance was unknown. Swine from each herd were randomly selected, humanely euthanized and spleens and samples of small intestine were removed. DNA was extracted from splenic tissue and used in a PCR-RFLP assay described in Example 1. Intestinal cells were purified by scraping the mucosal surface off the intestine, lysing the cells in a hypotonic EDTA solution and washing by centrifugation. The purified intestinal cell brush borders were incubated with F18 *E. coli*. This mixture was examined by phase contrast microscopy. This assay determined if swine were susceptible (intestinal samples had adhering bacteria) or resistant (intestinal samples had no adhering bacteria). The PCR-RFLP assay for the polymorphism correlated with the bacteria-intestinal cell binding assay in 53 of 53 resistant swine and 128 of 130 susceptible swine. Two swine that were determined susceptible using the bacteria-intestinal cell binding assay were incorrectly predicted to be resistant using the PCR-RFLP assay. Two of the six herds examined contained resistant pigs, while only one herd had porcine stress syndrome, demonstrating that the PCR-RFLP assay can identify disease resistant animals in animals that do not have porcine stress syndrome.

Example 3

Localization Of FUT1 On Chromosome 6 (SSC6)

Cosmids ETHs1, -s2, -s3, -s4 and -s6 were identified after screening of the cosmid library with a FUT1 nucleotide probe obtained from porcine genomic DNA with primers P7 and P10 and were mapped by FISH and DISC-PCR to chromosome 6 in band q11.

Example 4

Identification of the Porcine FUT1 ORF

Hybridizing KspI, EcoRI and KspI/EcoRI cosmid digests with radiolabelled porcine FUT1 fragments P6–P11 and P7–P10 for Southern blot analysis revealed identical autoradiography signals for ETHs2, -s4 and -s6, whereas different signals were obtained from cosmids ETHs1 and -s3. From cosmid ETHs2 KspI, subclones 940 bp and 6.2 kb in length were isolated, corresponding to the estimated length of hybridizing KspI fragments on the Southern blot. The sequence results of both subclones were combined to yield a 1501 bp sequence, which was in agreement with results of direct sequencing of genomic PCR products. The 1501 bp sequence contains an open reading frame (ORF) of 1098 bp corresponding to the human FUT1 ORF, with 82.3% nucleotide and 80.8% amino acid identity. The ORF encodes a polypeptide.

Example 5

Identification of a Porcine FUT2 and a Pseudogene FUTP

ETHs1 has one DNA fragment (2.7 kb) that hybridizes to FUT1 sequences, whereas ETHs3 has two (2.7 kb and 8.2 kb). Subcloning and partial sequencing of the 2.7 kb EcoRI fragment of ETHs1 and -s3 confirmed that these two fragments are identical. The sequence is highly similar to the human FUT2 but shows several changes in the NH$_2$— and —COOH terminal regions. These changes lead to frame shifts that are not compatible with a conserved ORF, therefore an assumption is that the sequence obtained from the 2.7 kb fragment represents a psuedogene (FUT2P). After subcloning of ETHs3 BamHI digests, the hybridizing sequences contained in the 8.2 kb EcoRI fragment were identified. The sequence of the subclones obtained represents a 1023 bp ORF and is 85% identical at the nucleotide- and 83% identical at the amino acid level to the human FUT2 sequence. Many differences in the NH$_2$— and —COOH terminal regions were observed between the porcine FUT2 sequence and the FUT2P sequence derived from the 2.7 kb fragment. The predicted amino acid sequence corresponds to the partially determined amino acid sequence of the porcine Secretor enzyme (Thurin and Blaszczyk-Thurin, 1995). The porcine FUT1, FUT2 and FUTP sequences obtained were submitted to GenBank and have accession numbers U70883, U70881 and U70882, respectively. The FUT1 and FUT2 genes have highly homologous sequences. This has to be considered in, for example, primer development. Furthermore, FUT1 and FUT2 enzyme activity need to be differentiated in further studies.

Example 6

Identification of M307 and M857 Mutations and Characterization of M307

DNA was isolated from porcine nucleated cells according to standard procedures. Direct sequencing of porcine FUT1 and FUT2 sequences and their flanking regions in animals of different ECF18R genotypes (Bb, bb) resulted in the identification of two G→A transitions at positions 307 and 857 (termed M307 and M857, respectively) of the FUT1 ORF. The M307 transition eliminates a restriction site for the enzyme CfoI. Amplification of DNA isolated from porcine nucleated cells was performed according to standard procedures with primers P6 and P11 (3 min at 95° C., 30 cycles of 30 sec at 95° C., 30 sec at 56° C. and 30 sec at 72° C., followed by a 7 min final extension at 72° C.) followed by CfoI digestion and separation on a 3% agarose gel resulted in a restriction fragment length polymorphism (RFLP). Homozygous M307$^{AA}$ animals showed 2 bands (93- and 328-bp fragments). Homozygous M307$^{GG}$ animals showed 87-, 93-, and 241-bp fragments. Heterozygous animals showed all four fragments.

Example 7

Characterization Of Mutation M857

The M857 mutation is a transition that eliminates an AciI site. Primer PBEST was designed to mismatch two additional AciI sites at positions 866 and 872. PCR with primers P7 and PBEST (3 min at 95° C., 30 cycles of 30 sec at 95° C., 30 sec at 56° C. and 30 sec at 72° C., followed by a 7 min final extension at 72° C.) followed by AciI digestion enables PCR-RFLP analysis on a 3% agarose gel. Homozygous M857$^{AA}$ animals show a 174 bp fragment while amplification products of M857$^{GG}$ animals show 136- and 38-bp fragments.

Example 8

Genetic Mapping Of The FUT1 Gene

In Landrace swine families, recombination events between M307 and the loci of the HAL linkage group (S, ECF18R, RYR1, GPI, PGD) revealed recombination fractions θ<0.04 (Table 2). The lodscores Z for the overall recombination fractions were between 24.5 and 50.6, showing strong evidence for linkage between these loci. These data allow genetic mapping of the FUT1 gene to the HAL linkage group in close proximity of S and ECF18R which are both influenced by FUT1. In the experimental Landrace families, allelic association was found between ECF18R and RYR1. An excess of genotypes RYR1$^{TT}$ at position 1843 in RYR1 (halothane susceptible genotype) was observed among pigs resistant to oedema disease and postweaning diarrhea (genotype ECF18R$^{b/b}$) (Table 3). This allelic association is a result of linkage disequilibrium, that is, deviation of observed haplotype frequencies from expected haplotype frequencies under independent assortment of alleles. Therefore, linkage disequilibrium designates a non random association of alleles belonging to linked loci. Owing to low recombination rates however, no locus order could be determined as being significantly better than others.

Example 9

Association Of M307$^A$ With ECF18$^b$ And M307$^G$ With ECF18R$^B$

In Landrace (SL) and Large White (LW) parental pigs, ECF18R$^b$ (the oedema and postweaning diarrhea resistance allele) is 100% associated with M307$^A$, and ECF18R$^B$ (the oedema and postweaning diarrhea susceptibility allele) is 100% associated with M307$^G$ (wherein A=adenine; G=guanine). In SL pigs 88% (30/34) of S$^s$ accounted for all ECF18R$^b$ and M307$^A$ haplotypes, respectively. The corresponding values for both the S$^s$-ECF18R$^b$ and S$^s$-M307$^A$ haplotypes were 82% (9/11) in Large White pigs. In the experimental SL families, the occurrence of the M857$^A$ allele at the FUT1 locus was low, and even absent, in LW pigs. Therefore, a significant gametic association was not observed between the alleles of M857 and the alleles of the flanking genes. The G→A transitions at positions FUT1 307 and FUT1 857 were found with variable frequencies also in Duroc, Hampshire and Pietrain pigs, making it likely that those transitions also occur in other pig breeds.

Example 10

Distribution Of FUT1 Genotypes

Table 4 shows that the distribution of FUT1 genotypes at nucleotide position 307 among ECF18R types was significantly different from the expected ratio under a hypothesis that the two are independent. Of the 119 oedema disease and postweaning diarrhea resistant ECF18R$^{b/b}$ animals, 118 were determined to have the genotype M307$^{AA}$ in the DNA-based test. One resistant animal had the genotype M307$^{A/G}$. Of the 131 susceptible pigs, 130 were M307$^{A/G}$ or M307$^{G/G}$. One animal, susceptible to E. coli adhesion, was shown to be homozygous M307$^{A/A}$ by the DNA-test. The data from this example and example 2, together with past studies suggested that the FUT1 gene is the gene present at the S locus in swine and the ECF18 locus. While 4 animals in this example and example 2 contradict this hypothesis, it is probable these animals were incorrectly phenotyped in regards to disease resistance/susceptibility.

Example 11

Amino Acid Exchanges in Alpha (1,2) Fucosyltransferase

The G→ changes at bp +307 and bp +857 of the alpha (1,2) fucosyltransferase gene 1 results in a predicted amino acid substitution of threonine (neutral-polar) instead of alanine (neutral-nonpolar) and glutamine (neutral-polar) instead of arginine (basic), respectively which may have functional consequences in the encoded product. A C→T change at bp 229 results in an amino acid substitution of leucine (neutral-nonpolar) instead of phenylalanine (neutral-nonpolar).

TABLE 1

Sequences Of Forward-(F) And Reverse-(R) Primers And Their Relative Position To The Porcine FUT1 And FUT2 Start Codons.[2]

| Primer name | Primer sequence | Position |
| --- | --- | --- |
| FUT1 P6 (R) | 5'-CTTCAGCCAGGGCTCCTTTAAG-3' (SEQ ID NO:3) | +489 |
| FUT1 P7 (F) | 5'-TTACCTCCAGCAGGCTATGGAC-3' (SEQ ID NO:4) | +720 |
| FUT1 P10 (R) | 5'-TCCAGAGTGGAGACAAGTCTGC-3' (SEQ ID NO:5) | +1082 |
| FUT1 P11 (F) | 5'-CTGCCTGAACGTCTATCAAGATC-3' (SEQ ID NO:6) | +69 |
| FUT1 P16 (F) | 5'-AGAGTTTCCTCATGCCCACAGG-3' (SEQ ID NO:7) | −90 |
| FUT1 P18 (R) | 5'-CTGCTACAGGACCACCAGCATC-3' (SEQ ID NO:8) | +1203 |
| FUT1 PBEST (R) | 5'-ACCAGCAGCGCAAAGTCCCTGAC GGGCACGGCCTC-3' (SEQ ID NO:9) | +893 |
| FUT2 P16 (R) | 5'-CTCCCTGTGCCTTGGAAGTGAT-3' (SEQ ID NO:10) | +1094 |
| FUT2 P17 (F) | 5'-AACTGCACTGCCAGCTTCATGC-3' (SEQ ID NO:11) | −83 |

[2]Primers FUT1 P10 and FUT1 P11 are derived from the human FUT1 gene.

TABLE 2

Overall Recombination Fractions (θ), Lodscores (Z) And Number Of Informative Animals (N) For M307 And Loci Of The HAL Linkage Group In The Landrace Experimental Population

| Locus pair | N | θ | Z |
| --- | --- | --- | --- |
| S-ECF18R | 183 | 0.01 | 50.6 |
| M307-S | 183 | 0.01 | 50.6 |
| M307-ECF18R | 216 | 0.01 | 57.1 |
| M307-RYR1 | 198 | 0.02 | 47.2 |
| M307-GPI | 147 | 0.03 | 34.2 |
| M307-PGD | 147 | 0.04 | 24.5 |

TABLE 3

Haplotype Frequencies At The Four Loci (S-FUT-1 (M307, M857)-ECF18R-RYR1) In The Landrace (SL) Experimental Population And Randomly Selected Large White (LW) Pigs.

| Breed | Haplotype[3] at S, FUT1 (M307, M857), ECF18R, RYR1 | Frequency[4] (number) |
| --- | --- | --- |
| SL | sAGbT | 70 (28) |
|  | sAGbC | 5 (2) |
|  | SGGBC | 15 (6) |
|  | sGABC | 10 (4) |
| LW | sAGbC | 56 (9) |
|  | SGGBC | 31 (5) |
|  | sGGBC | 13 (2) |

[3]S: Suppressor locus for A and O blood types (S and s). FUT1 (M307): alteration of adenine (A) to guanine (G) at nucleotide 307 of the alpha (1,2) fucosyltransferase (FUT1) gene. FUT1 (M857): alteration of adenine (A) to guanine (G) at nucleotide 857 of the FUT1 gene. ECFl8R: E. coli F18 receptor. The dominant susceptible allele is indicated by B and the resistant allele by b. RYR1: skeletal muscle ryanodine receptor. C (cytosine) is the dominant resistant and T (thymine) the susceptible allele for malignant hyperthermia.
[4]Haplotype frequencies in % and absolute number of haplotypes between brackets.

TABLE 4

Distribution Of The Genotypes, Tetrachoric Correlation (R) And Significance Of The Association ($\chi^2$ And w x $\chi^2$) Of The Associated Polymorphic FUT1 (M307) And ECF18R Loci In Landrace (SL) Experimental Population And Randomly Selected Large White (LW) Swine.

| Breed | Locus | FUT1/M307 Genotype | A/G | A/A | r | $\chi^2$ | $\chi^{2\,\text{x w5}}$ |
| --- | --- | --- | --- | --- | --- | --- | --- |
| SL | ECF18R[6] | b/b | 1 | 113 | 0.98 | 213.1 | 42.6*** |
|  |  | B/b | 106 | 1 |  |  |  |
| | | Genotype (A/G) | A/G G/G | A/A | | | |
| LW | ECF18R[6] | b/b | 0 | 5 | 1.00 | 29.0 | 11.6*** |
|  |  | B/b,B/B | 24 | 0 |  |  |  |

[5]A weight factor of w = 0.2 (SL) and 0.4 (LW) was applied to correct for the lack of percision resulting from inclusion of related animals in the data, according to Cotterman (1947).
***p < 0.001.
[6]Animals of genotype b/b at the ECF18R locus are resistant and those of genotype B/b and B/B are susceptible to adhesion of F18ab E. coli bacteria.

METHODS

1. Primers

Primers derived from the human FUT1 gene were used for the amplification of its porcine counterpart from genomic DNA. From the resulting porcine sequences specific primers were designed which were used in further amplification and sequencing reactions (Table 1).

2. Screening of a Porcine Genomic Library

Porcine genomic libraries were screened with either a porcine FUT1 probe obtained with primers P7 and p10 or a porcine FUT1 cDNA. A porcine genomic library, constructed in SuperCos 1 (Stratagene, La Jolla, Calif., USA), was screened with an $\alpha^{32}P$ dATP labeled (Prime It II, Stratagene) FUT1 probe obtained from porcine genomic DNA with primers P7 and P10. After hybridization of replica filters at 42° C. for 15 h (50% formamide, 6×SSC, 5×Denhardt's, 0.5% SDS, 0.1 mg/ml Salmon Sperm) and washing twice at 65° C. for 30 min. (1×SSC, 0.1% SDS), positive colonies were identified after exposure (15 h, −80° C.) to X-ray film.

3. In situ Hybridization of Porcine Metaphase Chromosomes

Cosmid clones ETHs1, ETHs2, ETHs3, ETHs4 and ETHs6 were subjected to fluorescence in situ hybridization (FISH) (Solinas Toldo, et al. 1993) or direct in situ chromosomal PCT (DISC PCR) on porcine metaphases. Metaphase chromosomes were Q-banded and photographed before hybridization. The probes were labeled by random priming using biotin-16-dUTP). Signal detection and amplification was performed using avidin-FITC and biotinylated anti-avidin. The chromosomes were counterstained with 4,6-diamidino-2-phenylindole, and the relative positions of the cosmids were determined as described by Solinas Toldo, 1993.

4. Subcloning

Enzymatic digests of probe positive genomic colonies were separated on agarose gel, transferred to a nylon membrane, and probe positive bands were subcloned into plasmids for FUT1 sequencing. The sequence of FUT1 derived from this method is shown in FIG. 1.

KspI-, EcoRI- and KspI/EcoRI digests of all cosmids were separated on a 0.8% agarose gel and transferred to a Hybond N nylon membrane. (Meijerink et al., 1997). This blot was hybridized with $\alpha^{32}P$ dATP labeled porcine FUT1 PCR products (primers P6–P11 and P7–P10). Based on the autoradiographic signals, ETHs1, -s2 and -s3 were subjected to further subcloning into pBluescript SK- (Stratagene), and FUT sequences were determined from subclones. The sequences of two FUT-like open reading frames (ORFs) (FUT1 and FUT2) obtained from cosmids ETHs2 and -s3 were compared in ECF18R positive (BB/Bb) and negative (bb) animals by direct sequencing of PCR products.

5. Polymerase Chain Reaction and Direct Sequencing

Using the Perkin Elmer Ready Reaction Dye Terminator kit (Perkin Elmer Cetus, Norwalk, Conn., USA) and 10 pmol of primer, cycle sequencing was performed with a thermal program consisting of an initial denaturation of 5 min at 95° C., followed by 25 cycles of 30 sec 95° C., 15 sec 50° C. and 4 min 60° C. Primers used for amplification and sequencing of the porcine alpha (1,2) fucosyltransferase genes are listed in Table 1. Additional primers were designed taking the possibility of cross-annealing of primers due to the high similarity of FUT1, FUT2 and the FUT2 pseudogene into account. Samples were analyzed on a 373A ABI sequencer (Applied Biosystems Inc.) and sequence analysis was performed with the GCG package (Devereux, 1984).

6. Production of Informative Offspring

Single nucleotide polymorphisms were analyzed in 221 Landrace swine produced from 4 boars and 16 sows, and in 29 Large White swine produced from 9 matings between unrelated swine. In order to produce a large number of informative offspring for the examination of linkage between porcine genes encoding ECF18 receptors and selected polymorphic loci, only informative Landrace matings of the type B/b×b/b were produced.

7. Colonization Test

In a study of Bertschinger et al., 1993, the above mentioned Landrace swine were also tested for ECF18 susceptibility in a colonization test. For this, swine were inoculated shortly after weaning with bacteria of E. coli strain 124/76 of serotype O139:K12(B):H1:F18. (Rippinger, et al., 1995). Faecal shedding of the bacteria was monitored daily. The extent of colonization was calculated as the mean of the two highest faecal scores. Swine with a mean faecal score of 3.5, corresponding to 6.7 log colony forming units (CFU)/g or more, were considered susceptible to colonization. This limit was based on a lack of mortality below this value, and on scores obtained from completely resistant litters.

8. Linkage Analysis of Nucleotide Polymorphisms

The results of the single nucleotide polymorphisms were compared with typing data for ECF18R, which were identified in an in vitro adhesion assay described by Vögeli et al., (1996), and with typing data for the GPI-, PGD-, α-1-B-glycoprotein-(A1BG), ryanodine receptor (RYR1), EAH- and S-loci as published by Vögeli et al. (1996). Pairwise linkage analysis and calculation of recombination fractions was performed using the CRI-MAP version 2.4 programme (Green et al., 1990). Multipoint linkage analysis was performed by sequential insertion of the above loci into the map. Haplotype frequencies were calculated from the parental animals, in the Landrace families and from the 8 parental Large White animals which were haplotyped for ECF18R from progeny information. Tetrachoric correlations of ECF18R and mutations in FUT1 (FUT1/M307) (polymorphisms) were calculated on all Landrace and Large White progeny.

9. Southern Blot Analysis

Southern blot analysis was performed of cosmids ETHs1 (1–3), ETHs2 (4–6) and ETHs3 (7–9) after digestion with enzymes KspI (1, 4, 7), EcoRI (2, 5, 8) and KspI/EcoRI (3, 6, 9) and separation on 0.8% agarose. Hybridization with an $\alpha^{32}$ PdATP labeled 5' FUT1 fragment (primers P6–P11) results in the same hybridizing 940 bp band in both the KspI digest (lane 4) and the KpsI/EcoRI digest (lane 6). However, hybridization with a 3' FUT1 fragment (primers P7–P10) (Table 1) shows a 6.2 kb KspI band in lane 4 and a 1.1 kb KspI/EcoRI band in lane 6. Both the 5' and 3' FUT1 fragments hybridize to the same 4.6 kb EcoRI fragment in lane 5. This indicates the presence of a KspI site in the FUT1 gene contained in cosmid ETHs2. Cross hybridization of the 3' FUT1 fragment detects 2.7 kb (lanes 2, 3, 8 and 9) and 8.2 kb (lanes 8 and 9) bands, resulting in the identification of the FUT2 pseudogene (incomplete ORF) and the FUT2 gene sequences, respectively.

10. Restriction Fragment Polymorphisms

Detection of (A) the M307 G to A and (B) the M857 G to A mutation in the porcine FUT1 gene was achieved by restriction length polymorphism analysis, using various restriction enzymes. Digestion of amplified FUT1 fragments with CfoI (A) and AciI (B) results in a restriction fragment polymorphism. In the first lane is a 100 bp marker. Fragment lengths are indicated in base pairs. (A) The M307$^{A/A}$ genotype (lane 2) generates 328 and 93 bp restriction fragments while the M307$^{G/G}$ genotype (lane 4) generates 93, 241 and 87 bp fragments and heterozygous M307$^{A/G}$ genotypes (lane 3) shows all four fragments.

(B) Digestion of the M857$^{A/A}$ genotype (lane 2) generates 174 bp fragments, while it generates 136 and 38 bp fragments in the M857$^{G/G}$ genotypes (lane 4), and in M857$^{A/G}$ genotypes (lane 3) all three fragments are generated.

11. Source of Swine

Data of the Swiss Landrace experimental population came from two pedigrees, which were built up at the Institute of Veterinary Bacteriology, University of Zurich. All other pigs of the Large White, Swiss Landrace, Duroc, Hampshire and Pietrain breeds came from different breeding herds of Switzerland. Other swine were randomly obtained from farms in the U.S. Midwest.

DOCUMENTS CITED

Bertschinger et al. (1993) Veterinary Microbiology 35:79–89.

Cohney et al. (1996) Immunogenetics 44:76–79.

Devereux et al., (1984) Nucleic Acids Res. 1:387–395.

Fujii et al. (1991) Science 253:448–451.

Green, et al., (1990) Documentation for CRI-MAP, Version 2.4, St. Louis: Washington University School of Medicine.

Kelly et al. (1994), Proc. Natl. Acad. Sci., U.S.A. 91:5843–5847

Meijerink, E. et al. (1997), 25th Int. Conf. on Animal Genetics, p. 44.

Rippinger, et al. (1995) Vet. Microbial. 45:281–295.

Solinas Toldo et al. (1993) *Mamm. Genome* 4:720–727.
Thurin and Blaszczyk-Thurin, (1995) *J. Biol. Chem.* 270 (44):26577–26580.
Vögeli et al. (1996) *Animal Genetics* 27:321–328
Vögeli et al. (1997) *Schweiz. Arch. Tierheilk.* 139:479–484.

U.S. Pat. No. 5,358,649, Maclennon et al.
U.S. Pat. No. 5,552,144, Valery et al.
WO 8604604 987P, Inventor: Peterson.
WO 9628967, Inventor: Koike, C.
WO 9413811, Inventors: Imberechts and Lintermans.
TW 266264, Inventors: Jeng and Liou.

We claim:

1. A method for identifying a swine that is resistant to F18 *Escherichia coli* associated intestinal disorders, said method comprising:

(a) determining in a biological sample from the swine whether the only nitrogen base at position 307 in the open reading frame of the alpha (1,2) fucosyltransferase gene 1, SEQ ID NO:12 is adenine; and (b) identifying the swine as resistant if the only nitrogen base at position 307 is adenine.

* * * * *

SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 1
ccaacgcctc cgattcctgt                                          20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 2
gtgcatggca ggctggatga                                          20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 3
cttcagccag ggctccttta ag                                       22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 4
ttacctccag caggctatgg ac                                       22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 5
tccagagtgg agacaagtct gc                                       22

<210> SEQ ID NO 6
<211> LENGTH: 23
<212> TYPE: DNA
<213> ORGANISM: Artificial Sequence

```
<220> FEATURE:
<223> OTHER INFORMATION: Description of Artificial Sequence: Primer

<400> SEQUENCE: 6
ctgcctgaac gtctatcaag atc                                             23

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 7
agagtttcct catgcccaca gg                                              22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 8
ctgctacagg accaccagca tc                                              22

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 9
accagcagcg caaagtccct gacgggcacg gcctc                                35

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 10
ctccctgtgc cttggaagtg at                                              22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
aactgcactg ccagcttcat gc                                              22

<210> SEQ ID NO 12
<211> LENGTH: 1269
<212> TYPE: DNA
<213> ORGANISM: Porcine
<220> FEATURE:
<221> NAME/KEY: CDS
<222> LOCATION: (9)..(1103)

<400> SEQUENCE: 12 ctcgagcc atg tgg gtc ccc agc cgc cgc cac ctc tgt ctg acc ttc ctg    50
```

-continued

```
            Met Trp Val Pro Ser Arg Arg His Leu Cys Leu Thr Phe Leu
              1               5                  10 cta gtc tgt gtt tta gca gca att ttc ttc ctg aac gtc tat caa gac    98
Leu Val Cys Val Leu Ala Ala Ile Phe Phe Leu Asn Val Tyr Gln Asp
 15              20                  25                  30 ctc ttt tac agt ggc tta gac ctg ctg gcc ctg tgt cca gac cat aac   146
Leu Phe Tyr Ser Gly Leu Asp Leu Leu Ala Leu Cys Pro Asp His Asn
             35                  40                  45 gtg gta tca tct ccc gtg gcc ata ttc tgc ctg gcg ggc acg ccg gta   194
Val Val Ser Ser Pro Val Ala Ile Phe Cys Leu Ala Gly Thr Pro Val
         50                  55                  60 cac ccc aac gcc tcc gat tcc tgt ccc aag cat cct gcc tcc ttt tcc   242
His Pro Asn Ala Ser Asp Ser Cys Pro Lys His Pro Ala Ser Phe Ser
             65                  70                  75 ggg acc tgg act att tac ccg gat ggc cgg ttt ggg aac cag atg gga   290
Gly Thr Trp Thr Ile Tyr Pro Asp Gly Arg Phe Gly Asn Gln Met Gly
 80                  85                  90 cag tat gcc acg ctg ctg gcc ctg gcg cag ctc aac ggc cgc cag gcc   338
Gln Tyr Ala Thr Leu Leu Ala Leu Ala Gln Leu Asn Gly Arg Gln Ala
 95                 100                 105                 110 ttc atc cag cct gcc atg cac gcc gtc ctg gcc ccc gtg ttc cgc atc   386
Phe Ile Gln Pro Ala Met His Ala Val Leu Ala Pro Val Phe Arg Ile
                115                 120                 125 acg ctg cct gtc ctg gcg ccc gag gta gac agg cac gct cct tgg cgg   434
Thr Leu Pro Val Leu Ala Pro Glu Val Asp Arg His Ala Pro Trp Arg
            130                 135                 140 gag ctg gag ctt cac gac tgg atg tcc gag gat tat gcc cac tta aag   482
Glu Leu Glu Leu His Asp Trp Met Ser Glu Asp Tyr Ala His Leu Lys
            145                 150                 155 gag ccc tgg ctg aag ctc acc ggc ttc ccc tgc tcc tgg acc ttc ttc   530
Glu Pro Trp Leu Lys Leu Thr Gly Phe Pro Cys Ser Trp Thr Phe Phe
160                 165                 170 cac cac ctc cgg gag cag atc cgc agc gag ttc acc ctg cac gac cac   578
His His Leu Arg Glu Gln Ile Arg Ser Glu Phe Thr Leu His Asp His
175                 180                 185                 190 ctt cgg caa gag gcc cag ggg gta ctg agt cag ttc cgt cta ccc cgc   626
Leu Arg Gln Glu Ala Gln Gly Val Leu Ser Gln Phe Arg Leu Pro Arg
                195                 200                 205 aca ggg gac cgc ccc agc acc ttc gtg ggg gtc cac gtg cgc cgc ggg   674
Thr Gly Asp Arg Pro Ser Thr Phe Val Gly Val His Val Arg Arg Gly
            210                 215                 220 gac tat ctg cgt gtg atg ccc aag cgc tgg aag ggg gtg gtg ggt gac   722
Asp Tyr Leu Arg Val Met Pro Lys Arg Trp Lys Gly Val Val Gly Asp
            225                 230                 235 ggc cgt tac ctc cag cag gct atg gac tgg ttc cgg gcc cga tac gaa   770
Gly Arg Tyr Leu Gln Gln Ala Met Asp Trp Phe Arg Ala Arg Tyr Glu
            240                 245                 250 gcc ccc gtc ttt gtg gtc acc agc aac ggc atg gag tgg tgc cgg aag   818
Ala Pro Val Phe Val Val Thr Ser Asn Gly Met Glu Trp Cys Arg Lys
255                 260                 265                 270 aac atc gac acc tcc cgg ggg gac gtg atc ttt gct ggc gat ggg cgg   866
Asn Ile Asp Thr Ser Arg Gly Asp Val Ile Phe Ala Gly Asp Gly Arg
                275                 280                 285 gag gcc gcg ccc gcc agg gac ttt gcg ctg ctg gtg cag tgc aac cac   914
Glu Ala Ala Pro Ala Arg Asp Phe Ala Leu Leu Val Gln Cys Asn His
            290                 295                 300 acc atc atg acc att ggc acc ttc ggc ttc tgg gcc gcc tac ctg gct   962
Thr Ile Met Thr Ile Gly Thr Phe Gly Phe Trp Ala Ala Tyr Leu Ala
            305                 310                 315
```

-continued

```
ggt gga gat acc atc tac ttg gct aac ttc acc ctg ccc act tcc agc         1010
Gly Gly Asp Thr Ile Tyr Leu Ala Asn Phe Thr Leu Pro Thr Ser Ser
320                 325                 330 ttc ctg aag atc ttt aaa ccc gag gct gcc ttc ctg ccc gag tgg gtg         1058
Phe Leu Lys Ile Phe Lys Pro Glu Ala Ala Phe Leu Pro Glu Trp Val
335                 340                 345                 350 ggc att aat gca gac ttg tct cca ctc cag atg ttg gct ggg cct             1103
Gly Ile Asn Ala Asp Leu Ser Pro Leu Gln Met Leu Ala Gly Pro
            355                 360                 365 tgaaccagcc aggagccttt ctggaatagc ctcggtcaac ccagggccag cgttatgggt       1163
ctccggaagc ccgagtaact tccggagatg ctggtggtcc tgtagcaggc tggacactta       1223
tttcaagagt gattctaatt ggctggactc agaggaaacc ctgcag                      1269
```

<210> SEQ ID NO 13
<211> LENGTH: 365
<212> TYPE: PRT
<213> ORGANISM: Porcine

<400> SEQUENCE: 13

```
Met Trp Val Pro Ser Arg Arg His Leu Cys Leu Thr Phe Leu Leu Val
 1               5                  10                  15

Cys Val Leu Ala Ala Ile Phe Phe Leu Asn Val Tyr Gln Asp Leu Phe
                20                  25                  30

Tyr Ser Gly Leu Asp Leu Leu Ala Leu Cys Pro Asp His Asn Val Val
            35                  40                  45

Ser Ser Pro Val Ala Ile Phe Cys Leu Ala Gly Thr Pro Val His Pro
        50                  55                  60

Asn Ala Ser Asp Ser Cys Pro Lys His Pro Ala Ser Phe Ser Gly Thr
65                  70                  75                  80

Trp Thr Ile Tyr Pro Asp Gly Arg Phe Gly Asn Gln Met Gly Gln Tyr
                85                  90                  95

Ala Thr Leu Leu Ala Leu Ala Gln Leu Asn Gly Arg Gln Ala Phe Ile
            100                 105                 110

Gln Pro Ala Met His Ala Val Leu Ala Pro Val Phe Arg Ile Thr Leu
        115                 120                 125

Pro Val Leu Ala Pro Glu Val Asp Arg His Ala Pro Trp Arg Glu Leu
130                 135                 140

Glu Leu His Asp Trp Met Ser Glu Asp Tyr Ala His Leu Lys Glu Pro
145                 150                 155                 160

Trp Leu Lys Leu Thr Gly Phe Pro Cys Ser Trp Thr Phe Phe His His
                165                 170                 175

Leu Arg Glu Gln Ile Arg Ser Gly Phe Thr Leu His Asp His Leu Arg
            180                 185                 190

Gln Glu Ala Gln Gly Val Leu Ser Gln Phe Arg Leu Pro Arg Thr Gly
        195                 200                 205

Asp Arg Pro Ser Thr Phe Val Gly Val His Val Arg Arg Gly Asp Tyr
210                 215                 220

Leu Arg Val Met Pro Lys Arg Trp Lys Gly Val Val Gly Asp Gly Arg
225                 230                 235                 240

Tyr Leu Gln Gln Ala Met Asp Trp Phe Arg Ala Arg Tyr Glu Ala Pro
                245                 250                 255

Val Phe Val Val Thr Ser Asn Gly Met Glu Trp Cys Arg Lys Asn Ile
            260                 265                 270

Asp Thr Ser Arg Gly Asp Val Ile Phe Ala Gly Asp Gly Arg Glu Ala
        275                 280                 285
```

-continued

```
Ala Pro Ala Arg Asp Phe Ala Leu Leu Val Gln Cys Asn His Thr Ile
    290                 295                 300

Met Thr Ile Gly Thr Phe Gly Phe Trp Ala Ala Tyr Leu Ala Gly Gly
305                 310                 315                 320

Asp Thr Ile Tyr Leu Ala Asn Phe Thr Leu Pro Thr Ser Ser Phe Leu
                325                 330                 335

Lys Ile Phe Lys Pro Glu Ala Ala Phe Leu Pro Glu Trp Val Gly Ile
            340                 345                 350

Asn Ala Asp Leu Ser Pro Leu Gln Met Leu Ala Gly Pro
        355                 360                 365
```